(12) United States Patent
Kegler

(10) Patent No.: US 6,635,659 B1
(45) Date of Patent: Oct. 21, 2003

(54) TOPICAL FORMULATION FOR ARTHRITIC SYMPTOMS TREATMENT

(76) Inventor: Arrie Kegler, 2640 Almeda Dr., Dallas, TX (US) 75216

( * ) Notice: Subject to any disclaimer, the term of this patent is extended or adjusted under 35 U.S.C. 154(b) by 0 days.

(21) Appl. No.: 08/639,486

(22) Filed: Apr. 29, 1996

Related U.S. Application Data

(63) Continuation-in-part of application No. 08/378,791, filed on Mar. 20, 1995, now abandoned.

(51) Int. Cl.$^7$ ............................................. A01N 43/40
(52) U.S. Cl. ...................................................... 514/320
(58) Field of Search ................................. 514/825, 625, 514/627; 424/195

(56) References Cited

U.S. PATENT DOCUMENTS

| | | | | |
|---|---|---|---|---|
| 4,271,154 A | * | 6/1981 | Richards | 424/195 |
| 4,440,760 A | | 4/1984 | Newnham | 424/184 |
| 4,540,709 A | | 9/1985 | Chang et al. | 514/470 |
| 4,704,279 A | | 11/1987 | Hancock | 424/195.1 |
| 4,832,946 A | | 5/1989 | Green | 424/70 |
| 4,877,615 A | | 10/1989 | Vandenbergh et al. | 424/115 |
| 4,939,149 A | * | 7/1990 | Blumberg | 514/691 |
| 5,167,957 A | | 12/1992 | Webb, Jr. et al. | 424/115 |
| 5,221,692 A | * | 6/1993 | Chen | 514/625 |
| 5,296,225 A | * | 3/1994 | Adekunle et al. | 424/195.1 |
| 5,500,205 A | * | 3/1996 | Abbott et al. | 424/401 |

FOREIGN PATENT DOCUMENTS

| | | | |
|---|---|---|---|
| CN | 35102253 | * | 9/1986 |
| FR | 2419682 | * | 10/1979 |
| WO | 9108738 | * | 6/1991 |

OTHER PUBLICATIONS

Li, Jiliang et al. Yunnan Daxue Xuebao, Ziran Kexueban (1994), 16(2), 153–6.*
Day, Robert et al. FR 2419682 abstract (1979) "Aromatic Oleoresin Emulsions" p. 13.*
Li, Jiliang et al. "Extraction of chili essence from Chili Peppers" (1994), 16(2), pp. 153–6.*
Pan, Chuhua et al. "Process for Extraction of Pepper Colors from Chilli oil", (1986) p. 6.*
"Study finds pepper ingredient eases surgical scar pain," *Dallas Morning News*, May 20, 1996.

* cited by examiner

*Primary Examiner*—Terressa M. Boykin
(74) *Attorney, Agent, or Firm*—Sidley Austin Brown & Wood LLP

(57) ABSTRACT

An extract made from peppers extracted with acetic acid under heat and pressure has been found effective for treatment of arthritic symptoms.

9 Claims, No Drawings

TOPICAL FORMULATION FOR ARTHRITIC SYMPTOMS TREATMENT

CROSS-REFERENCE

This is a continuation-in-part of co-pending U.S. Ser. No. 08/378,791 filed Mar. 20, 1995.

TECHNICAL FIELD

This invention relates to the field of topically applied formulation for treatment of arthritic pain.

BACKGROUND OF THE INVENTION

Many sufferers of arthritis experience intense pain in their joints, some of which can be of a debilitating nature. Solutions to the problem have included rubbing ointments or creams on the affected area or ingesting pharmaceuticals to help with the swelling which may occur.

Despite advances in medical science, many persons still suffer from such maladies as gout, joint and muscle aches, cramps, swelling, bursitis, and joint pain.

It has now been found that a new formulation for arthritis relief based on natural extracts from peppers can be topically applied to an affected area and provide relief to the patient.

SUMMARY OF THE INVENTION

An extract is made by selecting hot peppers and treating them with apple cider vinegar. Under heat and pressure, peppers are cooked in the apple cider vinegar, cooled to room temperature and the extract is filtered until free of all sediment. In another embodiment, the formula is topically applied to the skin of a patient in need of treatment. The area affected need be only lightly moistened with the composition.

DETAILED DESCRIPTION OF THE INVENTION

The formulation of the invention utilizes hot peppers extracted under certain conditions with apple cider vinegar. The peppers may be selected from the following types: Cayenne, Jalapeno, Serrano, and/or Habanero.

The solvent used in this invention is preferably apple cider vinegar of four or five percent acidity. While other vinegars may be used, it has been found that apple cider vinegar produces the most consistent extract in final formulation. A formulation of pure acetic acid of the appropriate strength may also be used. What is desired is that an effective amount of solvent be used to extract the peppers and to also serve as a carrier.

In manufacturing the pepper extract, approximately one gallon of apple cider vinegar is added to one pound of Cayenne, Jalapeno, or Serrano peppers. The peppers and vinegar are placed in a pressure cooker, allowed to boil for about one hour, and then cooled to room temperature. After cooling, the cooked peppers are removed and discarded. The remaining liquid is strained until it is free of all sediment.

With regard to Habanero peppers, it is most preferred that a half pound of peppers to a gallon of vinegar is utilized and boiled under pressure for approximately one hour. At this time the peppers are removed and the mixture allowed to cool to room temperature. The liquid is strained until it is free of all sediment, at which point the formulation is ready to be used or bottled as desired.

The amount of peppers to be used can vary depending on the potency of the final product desired. While it has been found that a ratio of one pound of Cayenne, Jalapeno or Serrano peppers is most effective to one gallon of Apple cider vinegar, the strength of the mixture can be decreased by using a lesser amount of peppers, or increased by using a greater amount of peppers.

It has been found that a ratio of one-half pound of Habanero peppers is most effective to approximately one gallon of apple cider vinegar. Again, however, the potency of the final solution can be varied by varying the amount of peppers to be used.

The extracted pepper solution can be utilized as an effective topical application for arthritis patients and those with similar adversities.

EXAMPLE ONE

Composition of Formulation

| | pH |
|---|---|
| Sample 22058-1 | 3.0 |
| Sample 22058-2 | 2.9 |
| Metal Content | |
| Heavy metals | none |
| Sodium | 310 mg per liter |
| potassium | 59 mg per liter |

EXAMPLE TWO

Use of Formulation on Patients

A formulation made according to the general description provided above produced the following results after topical application to the affected area.

TABLE 1

| Patient Number | Condition | Duration of Condition | Results |
|---|---|---|---|
| One | back pain, nonspecific arthritis | 25 years | pain relief |
| Two | nonspecific arthritis in back and leg, confined to bed | 8 years | able to walk and move about; relief from pain, swelling and stiffness |
| Three | osteoporosis in back, confined to bed | 25 years | relief from pain, swelling and stiffness; able to move about |
| Four | arthritic pain in legs | one year | relief |
| Five | arthritic pain in legs, confined to wheelchair for last year, lumbar radiolopathy, spinal stenosis and lumbar degenerative disc disease | 21 years | pain eliminated; ability to walk regained |
| Six | rheumatoid arthritis in the joints | 9+ years | relief of cramps, stiffness and joint pain |
| Seven | arthritis in joints and cramps | 25 years | relief of cramps and pain |
| Eight | rheumatoid arthritis | many years | outstanding |

TABLE 1-continued

| Patient Number | Condition | Duration of Condition | Results |
|---|---|---|---|
| | in knees, hip and back | | improvement reported |

EXAMPLE 3

Relief Over a Period of Time

A patient, aged 34, was treated and diagnosed by a doctor of chiropractic medicine. The patient complained of pain in both knees and legs over a period of four months. The patient characterized the pain as "four" on a scale or one to ten, but also that the pain had constant duration. The patient indicated that walking after sitting a long time and climbing stairs aggravated the condition. The patient reported that the condition was relieved by walking, riding a bike, and movement. The patient explained that initially there was swelling that occurred several times during prolonged periods of standing. The patient indicated he was on no medication and did not wear any type of support.

The patient was diagnosed with rheumatoid arthritis of the knees and the X-ray indicated slight swelling of soft tissue behind and along the medial and lateral knee. Tenderness and swelling were noted upon examining the knees and the patient was found to have a very restricted range of motion associated with moderate pain with passive motion.

A formula made according to the method of the invention was administered to the surface of the anterior and posterior knee joint. The patient noted relief within minutes. The patient was able to climb stairs within thirty minutes without complaint or of knee pain. The range of motion was substantially improved.

The next day the patient reported less swelling and that the joints felt more loose with more tolerable pain. Walking up the stairs was still painful. Ambulation was much improved and the patient was able to bend knees with little pain. The formula of the invention was typically administered to the affected area of the patient once again.

Eight days later, the patient reported that walking up the stairs did not cause any pain, that he no longer had stiffness in his knees, and that he felt ninety percent better. After thirty-eight days the patient reported that he no longer experienced any pain.

I claim:

1. A method of preparing a formulation for relieving symptoms of arthritis, consisting essentially of the steps of:

(a) pressure cooking by boiling a quantity of capsaicin-containing peppers under pressure sufficient to increase the boiling temperature of an extraction solvent to a point above its boiling point at atmospheric pressure, which extraction solvent comprises acetic acid, for a time period effective to extract said peppers to form a pepper mixture comprising a liquid portion and a sediment portion whereby active ingredients are leached out into said liquid portion; and (b) filtering the liquid portion from the sediment portion of said pepper mixture and retaining the liquid portion which comprises said formulation.

2. The method of claim 1 wherein said solvent is about 5% acetic acid and about 95% water.

3. The method of claim 1 wherein said acetic acid solvent is apple cider vinegar.

4. The method of claim 1 wherein said time period is about one hour.

5. A method of treating symptoms of arthritis, comprising:

applying a formulation, made according to the extraction method of pressure cooking by boiling a quantity of capsaicin-containing peppers under pressure sufficient to increase the boiling temperature of an extraction solvent to a point above its boiling point at atmospheric pressure, which extraction solvent comprises acetic acid, for a time period effective to extract said peppers and filtering the liquid from the sediment and retaining the liquid which comprises the formulation, topically to the area affected in amounts sufficient to cause a beneficial effect.

6. The method of claim 5 wherein said solvent is about 5% acetic acid and about 95% water.

7. The method of claim 5 wherein said acetic acid solvent is apple cider vinegar.

8. The method of claim 5 wherein said time period is about one hour.

9. A formulation for topical application to patients for treatment of arthritic symptoms, made according to the method of claim 1.

\* \* \* \* \*